July 16, 1957 H. M. TIRET Plant Pat. 1,620
FUCHSIA PLANT
Filed Oct. 2, 1956
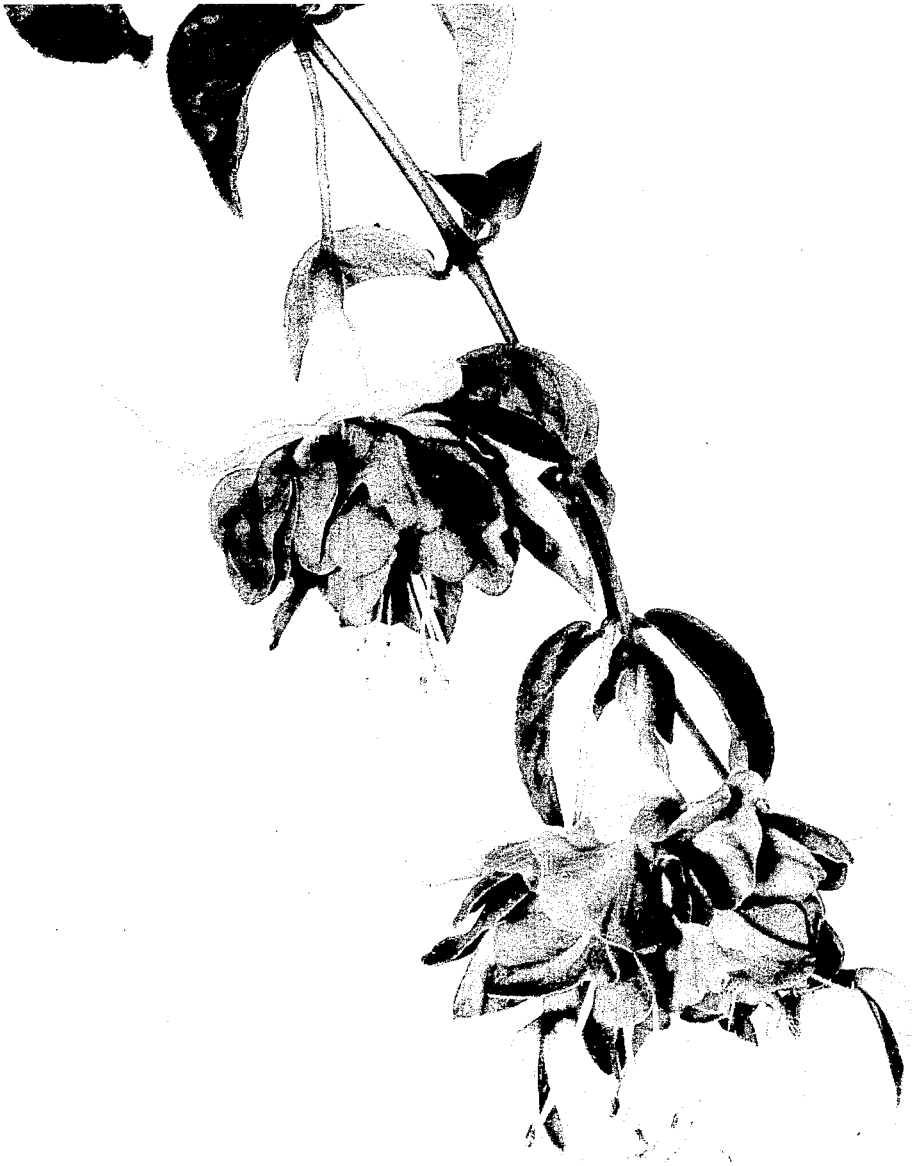

United States Patent Office

Plant Pat. 1,620
Patented July 16, 1957

1,620

FUCHSIA PLANT

Horace M. Tiret, San Francisco, Calif.

Application October 2, 1956, Serial No. 613,589

1 Claim. (Cl. 47—60)

This invention relates to a new and improved fuchsia plant, the principal new and different characteristic of which is the exceptional size of bloom combined with the classical symmetrical form, unlike any other fuchsia plant.

As a hybrid from Georgana, Plant Patent No. 1,501, and His Excellency (unpatented), the fuchsia plant is distinguished principally by the fact that this is a flower of extreme size which, combined with its form and growing habits, creates an appearance unlike any fuchsia of its type. The plant has been asexually reproduced at Colma, California, and Gardena, California, by cuttings which retained the characteristics of the parent fuchsia.

The plant is a vigorous, upright grower. It is a heavy bloomer for a plant producing such large flowers. The petals are Amethylst Violet (British Horticultural Color Chart #35) on the outside and Violet (British Horticultural Color Chart #36) on the inside. As the flower ages the petals acquire a new color, Orchid Purple, which is uniform to both sides (British Horticultural Color Chart #31). A few of the outer petals are marbled at the base, Fuchsine Pink (British Horticultural Color Chart #627/2).

In the accompanying drawing, the figure shows a typical branch tip, the drawing representing approximate actual size.

A detailed description of this new variety of fuchsia plant follows:

*Habit of growth.*—This is an upright variety, quite vigorous, and an early bloomer. It is very self-branching.

*Foliage.*—The leaves are dark green, medium in size, with a slightly veined surface. The mature leaf is approximately 2¾″ in length and 1¾″ in width at the widest point. The leaf is medium crinkly in texture. Branches are dark red.

*Buds.*—These are Phlox Pink (British Horticultural Color Chart #625/1). The length from ovary is approximately 2″. Width at widest point is 1¼″.

*Ovary.*—Solid green in color. Length ⅝″, width at widest point 5/16″, at maturity.

*Sepals.*—Four in number, 2″ in length, and 1″ in width at widest point. Form of sepals is broad and slightly recurved. Underside has crepe (slight) texture, outer side smooth and satiny texture.

*Tube.*—Medium short. Length is approximately ⅞″, width 7/16″ at widest point.

*Stamens.*—Eight in number, colored rose and deeper rose anthers. Medium slender, 2¼″ in length.

*Pistil.*—The style is approximately 2¾″ in length, 1/16″ in width, color rosy pink. The stigma is creamy white.

*Petals.*—The petals number 28 (approximately). They are exceptionally large, fully open corolla. The center petals are vertical and the outer petals horizontal, creating an extremely flaring form. The diameter of the fully open mature flower is approximately 4″. The large petals are approximately 1¾″ in length and width. They have a smooth appearance.

*Parentage.*—Georgana (patented) and His Excellency (unpatented).

Having thus disclosed my discovery, I claim:

A new and distinct variety of fuchsia plant herein described and illustrated, characterized by the exceptional size of the blooms, the classic symmetrical form, in conjunction with attractive coloring and excellent and vigorous growing habit which constitute a fuchsia unlike any other of its type.

No references cited.